(12) United States Patent
Wolfart et al.

(10) Patent No.: US 9,211,235 B2
(45) Date of Patent: Dec. 15, 2015

(54) REMOVABLE ADHESION MATERIAL

(75) Inventors: Stefan Wolfart, Aachen (DE); Andrij Pich, Aachen (DE)

(73) Assignee: Rheinisch-Westfaelische Technisch Hochschule Aachen, Aachen (DE)

( * ) Notice: Subject to any disclaimer, the term of this patent is extended or adjusted under 35 U.S.C. 154(b) by 0 days.

(21) Appl. No.: 14/118,942

(22) PCT Filed: May 18, 2012

(86) PCT No.: PCT/EP2012/059259
§ 371 (c)(1),
(2), (4) Date: Nov. 20, 2013

(87) PCT Pub. No.: WO2012/159987
PCT Pub. Date: Nov. 29, 2012

(65) Prior Publication Data
US 2014/0080097 A1    Mar. 20, 2014

(30) Foreign Application Priority Data
May 20, 2011   (EP) ..................... 11166855

(51) Int. Cl.
*A61K 6/00*    (2006.01)
*A61C 7/02*    (2006.01)
*A61C 13/15*   (2006.01)

(52) U.S. Cl.
CPC ............ *A61K 6/0002* (2013.01); *A61C 7/023* (2013.01); *A61C 19/003* (2013.01); *A61K 6/0023* (2013.01)

(58) Field of Classification Search
CPC .............................. A61K 6/0023; C08L 35/00
USPC .................. 523/118, 204; 433/228.1; 106/35
See application file for complete search history.

(56) References Cited

U.S. PATENT DOCUMENTS

| | | |
|---|---|---|
| 4,711,813 A | 12/1987 | Salyer |
| 4,747,240 A | 5/1988 | Voisinet et al. |
| 6,619,049 B1 | 9/2003 | Wu |
| 6,716,526 B2 * | 4/2004 | Weston et al. ............. 428/402.2 |
| 7,056,116 B2 * | 6/2006 | Scott et al. ...................... 433/29 |
| 7,575,628 B2 * | 8/2009 | Lu et al. ........................ 106/640 |
| 2007/0142498 A1 | 6/2007 | Brennan et al. |
| 2011/0108758 A1 | 5/2011 | Driscoll |

FOREIGN PATENT DOCUMENTS

WO    01/19420 A1   3/2001

* cited by examiner

*Primary Examiner* — Tae H Yoon
(74) *Attorney, Agent, or Firm* — Whitham, Curtis, Christofferson & Cook, P.C.

(57) ABSTRACT

The present invention relates in a first aspect to an adhesion material for use in an individual containing encapsulated phase-change material. In particular, the adhesion material is for cosmetical or medicinal use in the body of an individual. The adhesion material contains encapsulated phase-change material having preferably a phase transition temperature above 40° C., like above 55° C. The adhesion material is particularly useful for adhering elements, like dental restorations, e.g. crowns or bridge, or brackets on elements in the body of an individual, like teeth or implants. That is, the adhesion material is particularly useful for adhering material in dental applications. In another aspect, a method is provided allowing removing a bracket, a crown or bridge, from implants, abutments or teeth. Furthermore, dental implant restoration systems and kits for permanent fixation of implants allowing improved removal thereof are provided.

14 Claims, 1 Drawing Sheet

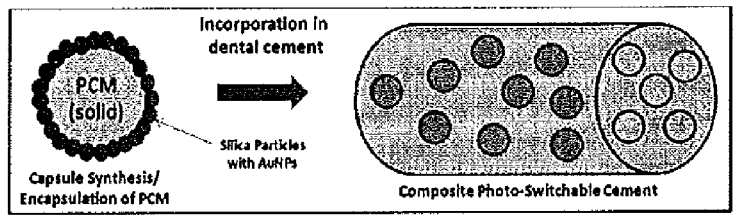
Fig. 1. Schematic representation of the removable adhesion material
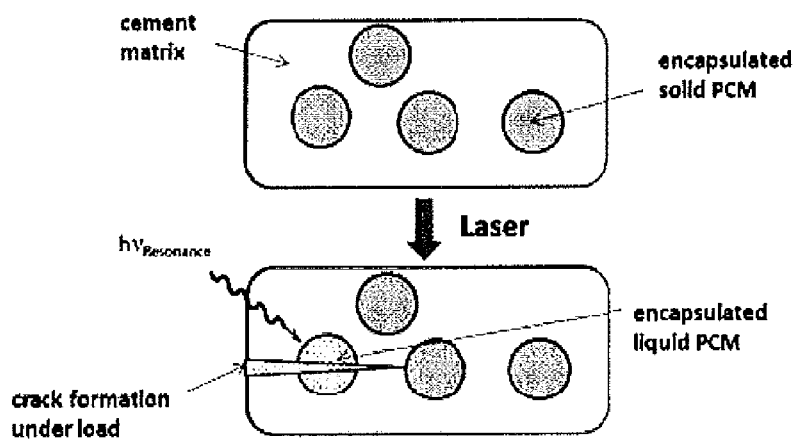
Fig. 2. Destruction of the removable adhesion material under laser irradiation.

REMOVABLE ADHESION MATERIAL

CROSS-REFERENCE TO RELATED APPLICATIONS

This application is a 371 application based on PCT/EP2012/059259 filed May 18, 2012.

The present invention relates in a first aspect to an adhesion material for use in an individual containing encapsulated phase-change material. In particular, the adhesion material is for cosmetical or medicinal use in the body of an individual. The adhesion material contains encapsulated phase-change material having preferably a phase transition temperature above 40° C., e.g. above 55° C. The adhesion material is particularly useful for adhering elements, like dental restorations, e.g. crowns or bridge, or brackets on elements in the body of an individual, like teeth or implants. That is, the adhesion material is particularly useful for adhering material in dental applications. In another aspect, a method is provided allowing removing a bracket, a crown or bridge, from implants, abutments or teeth. Furthermore, dental implant restoration systems and kits for permanent fixation of implants allowing improved removal thereof is provided.

BACKGROUND ART

At present, various materials are used as adhesives or adhesive agents also called bonding agents in various fields. For example, for use in individuals like mammals, in particular, in humans, various adhesives are described in the field of fixation of dental restorations or orthodontic applications on implants, abutments or teeth, as well as in other implant applications.

In dentistry cements are in principle divided in three groups, (1) provisional cements, (2) conventional cements and (3) adhesive luting materials (adhesive cements). (1) Provisional cements are used for a short period of time (up to 6 months) to fix provisional restorations on teeth or implants or implant-abutments. The cementation can be destroyed/loosen using nippers or special devices using an impulse which is transmitted to the provisional restoration. Normally the restoration can be removed without breaking the restoration. On the other hand these cements are not stabile over time and caries can appear on the abutment tooth or the restoration might get loose unpredictable.

(2) Conventional cements compose a hard layer between definitive restoration and the teeth, implants or implant-abutments. This layer is stable within the oral cavity over time and holds the restoration in place over years. There is no or only low chemical bonding between the cement and the materials of the restoration, the teeth, the implants or the implant-abutments. Normally the restoration can be removed from the teeth, implants or abutments only by destroying the restoration.

(3) The adhesive cementation has the same characteristics as the conventional cement, however there is an additional chemical adhesion to the different materials like tooth structures, implant and implant-abutment materials (for example titan, gold alloy, all-ceramic materials). Therefore this type of cementation is even stronger than the conventional cementation and it can be used even to fix less frictional type of elements (for example veneers, inlays), definitive splints for teeth or brackets.

In particular, for fixation of implants in dental applications, an adhesive luting is applied. Typically, dental cements are used for adhesion. Dental cements are permanent non-removable or provisional dental cements which are either resin cements or acid-based cements. Acid-based cements are typically in form of a powder of a basic metal oxide or silicate and an acidic liquid for hardening. Alternatively, resin-based cements are used in the field of dentistry and tooth restoration. Furthermore, non-aqueous acid-based cements like zinc oxide eugenol and non-eugenol zinc oxide are known. These non-aqueous acid-based cements contain metal oxide fillers embedded in a metal salt matrix. Dental cements are used for a variety of dental and orthodontic applications, including use as luting agents, pulp protecting agents or cavity-lining material. In addition, they are used to form an insulating layer under metal-ceramic or all-ceramic restorations and protect the pulp from injury.

Dental implants are alloplastic materials being provided in the area of the jaw bone. Said implants are used to fastening dental prosthesis. Typically, said implants are in two parts form composed of the implant body and the abutment. The abutment is fixed with the implant body by fastening means, e.g. by screwing. Restoration by crowns or bridges as permanent dental prosthesis is achieved by adhesion materials, like dental cement.

Until today, the dental cement used for fixation of prosthesis are designed for permanent fixation of the dental prosthesis. However, it is desired to allow removal of the dental prosthesis in case of technical and biological complications, e.g. clinical complications, or in case of ceramic chipping.

However, removal of the provisional or permanent restorations involves typically destruction or damage of the implant, abutment, abutment screw or restoration. Thus, reuse of the permanent restorations, e.g. the crowns and bridges, is hardly possible. Further, in case of the provisional fixation of a provisional restoration with adhesive materials designed for provisionals, the risk of an undesired loosening of the provisional may occur, thus, resulting in aspiration or swallowing of the provisional. On the other hand, permanent restorations may be removed only by destruction of the restoration. The destruction requires the complete restoration of the implant including new preparation of the restoration material.

Orthodontics brackets are adhesively cemented on the enamel of the teeth. When later the brackets have to be removed again, the brackets must be removed with special nippers. However there is adhesive cement remaining on the tooth structure, which has to be removed with diamond or hard metal burs in a second step. This procedure is time consuming and there is always the risk to remove not only the adhesive material, but also part of the tooth structure, Hence, there is a need for a new adhesive material allowing permanent fixation of second elements, like restorations on first elements present in the body of the patient, like implants or teeth, in particular for dental and orthodontic applications, allowing a removal of the means, like restorations or dental applications without destruction of the first and second elements fixed on each other like restorations, teeth or implants.

BRIEF DESCRIPTION OF THE PRESENT INVENTION

The present invention provides new adhesion materials for use in an individual allowing permanent fixation of the elements to be fixed. Said adhesion material is characterised in containing encapsulated phase-change material. Preferably, said phase-change material is a phase-change material having a phase transition temperature above 55° C. Said adhesion material is particularly useful as a dental cement for allowing controlled adhesion in the field of implant restorations and other dental applications.

That is, the adhesion material is particularly for cosmetic or medicinal use in individuals and in particular in dental and orthodontic application.

Preferably, the adhesion material is a dental cement allowing fixation of crowns and bridges but also brackets on the implant or the teeth, accordingly.

In a preferred embodiment the dental cement is a phosphate-based cement.

In addition, a method for removing the fixed elements, like a definitive cemented restoration or bracket is provided. Said method includes the weakening of the adhesion material adhering the elements with each other, like the restoration material or the brackets, with sufficient energy to heat the phase-change material present in the adhesion material according to the present invention above the phase transition temperature, thus, weakening the adherence properties of the adhesion material.

In addition, dental implant restoration systems as well as kits for permanent fixation of implants allowing removal of said implants containing the adhesion material according to the present invention are provided.

DETAILED DESCRIPTION OF THE PRESENT INVENTION

In a first aspect, the present invention relates to an adhesion material for use in an individual. Said adhesion material is characterised in containing encapsulated phase-change material. The phase-change material according to the present invention has preferably a phase transition temperature above 40° C., preferably, above 55° C.

That is, the present invention provides an adhesion material allowing removal of the adhered elements, e.g. of restoration in dental and orthodontic application. The adhesion material is for use in an individual, like mammals, in particular, for use in man.

In this connection, the term "for use in an individual" refers to medicinal, like prophylactic or therapeutic use including surgical use in an individual or subject. In addition, "for use in an individual" refers to non-medicinal use in an individual, e.g. cosmetic use.

The adhesion material is useful for mediating adherence between a first element present in the body of an individual and a second element to be fixed on said first element, optionally with an intermediate element.

As used herein, the term "first element" refers to an artificial or natural element present in the body of an individual. E.g., said first element is an implant, a tooth or bone.

As used herein, the term "second element" refers to an element that is going to be fixed to a first element. Said "second element" for example may be a restoration, e.g. a crown or bridge, or bracket. The second element may also be an orthopaedic implant. The second element may be fixed to the first element directly or with an intermediate element, like an abutment.

As used herein, the term "phase-change material" refers to material possessing the ability to change their state with a certain temperature range. These materials absorb energy during the heating process as phase change takes place, otherwise this energy can be transferred to the environment in the phase change range during a reverse cooling process. Phase change is the process of going from one physical state to another i.e. from a solid to a liquid and vice versa.

As used herein, the term "phase transition temperature" refers to a temperature where phase-change from solid to liquid occurs or where a remarkable change in viscosity from high viscosity to low viscosity occurs.

As used herein, the term "implant" refers to all types of means or devices used in the body of an individual unless otherwise indicated. In particular, the term includes material implanted or placed in the oral cavity. Other types of implants include artificial joints and other types of non-permanent implants implanted into the body of an individual.

Further, the term "dental prostheses" refers to second elements, like crowns, bridges, etc. The term also includes provisional dental prosthesis, brackets, or other materials to splint teeth permanent or semipermanent unless otherwise indicated.

The term "permanent" as used herein refers to the fixation effect that is usually achieved by conventional dental cements. The term "permanent" is used to stress that without laser irradiation at a certain wavelength this material behaves as conventional dental cement and is characterised by high compression strength, toughness, high density, high chemical resistance etc.

In a preferred embodiment, the present invention is an energy-switchable, like a photo-switchable dental cement that can be used for fixation of crowns on dental implants and can reduce its mechanical properties under illumination with laser light allowing fast, painless and non-destructive removal of the crown from the implant.

The present invention is based on a smart capsule containing phase change material. In particular, the smart capsule consists of a thin capsule wall that allows transformation of photon energy into thermal energy and the capsule core filled with a phase change material (PCM) able to undergo a phase transition (solid-liquid) upon heating. The coupling of both elements allows rapid transformation of solid core capsules into liquid core capsules under laser irradiation and thus considerable reduction of their mechanical properties. When such capsules are integrated as a filler into a solid matrix (dental cement), laser irradiation will induce rapid weakening of the composite material through formation of voids or cracks thus allowing destruction of the composite by application of mechanical force.

The adhesion material according to the present invention containing encapsulated phase-change material is preferably suitable for use in an individual. That is, said adhesion material may be used as adhesive for implants. The adhesion material is particularly useful for implants in the body of an individual.

That is, according to a preferred embodiment of the present invention, the adhesion material is an adhesion material for dental applications. Said adhesion material for dental application is preferably a cement, like a dental cement, for dental prosthesis. In particular, the cement is used for restoration applications in oral cavities.

The cement is useful for fixation of fixed dental prostheses (restorations) like crowns or bridges on implants or teeth. In addition, the adhesion material in form of a dental cement or as a polymeric adhesion material may be used for fixation of brackets, or other devices assisting in shaping the teeth and jaws. Today, removal of the cemented brackets of the braces is often very painful. The cement used for fixation of the brackets must be chipped and scrapped of which can cause severe pain in patients with sensitive teeth. Hence, the adhesion material according to the present invention represents useful cement for fixation of said brackets allowing easy removal.

Removal of the adhesion material according to the present invention can be achieved by heating locally the adhesion material over the phase transition temperature of the phase-change material. Thus, the phase-change material present in the adhesion material changes its consistence from e.g. solid to liquid. Consequently, weakening of the adhesive strength of the adhesion material is achieved, thus, allowing damage-free removal of the second element, like the restoration, from the first element, like the implant. In addition, an easy and, preferably, residue free removal of the adhesion material from the first and/or second element or the intermediate element is possible, which allows for re-use of said first and second elements.

The phase-change material is e.g. an encapsulated phase-change material. Encapsulation of the phase-change material prevents reaction of the phase-change material with the adhesive material, e.g. the polymer, e.g. during hardening of the adhesion material. In addition, mixing of the adhesive with the phase-change material is avoided. Moreover, encapsulation of the phase-change material improves to adjust the properties and characteristics of the adhesion material according to the present invention.

The adhesion material according to the present invention allows to remove the adhered materials, typically fixed dental prosthesis or material fixed in oral cavities or in other parts of the body, at a desired time point without destroying the adhered materials, thus, allowing re-use of said materials accordingly.

The encapsulated phase-change materials are e.g. encapsulated with inorganic silica. The size of the capsules is typically in the range of nanomolar or micromolar. For example, said capsules may have a size of 1 to 20 μm in diameter. In another preferred embodiment, the size of the capsules may be in the nm-range, e.g. in between 10 to 500 nm. The phase-change material is present in the core of said capsules only.

The skilled person is well aware of suitable phase-change materials. Typical phase-change materials include inorganic salts (sodium sulphate decahydrate ($Na_2SO_4 \times 10H_2O$, manganese(II) nitrate hexahydrate ($Mn(NO_3)_2 \times 6H_2O$; heat absorbing and -releasing temperature interval of up to 80° C.), suitable linear or branched hydrocarbons ($C_nH_{2n+2}$), fatty acids (capric, lauric, palmitic and stearic acids and their binary mixtures) and polymers (polyethylenglycols with variable molecular weight; melting point varies when molecular weight increases from 1000 g/mol to 20 000 g/mol).

The phase-change material has typically a melting or crystallisation temperature, i.e. a phase transition temperature of above 40° C., like above 45° C., eg. Above 50° C., in particular, above 55° C., preferably above 60° C., like above 65° C., or above 70° C. It is preferred that the phase transition temperature is in the range of from 55° C. to 100° C., e.g. 55° C. to 90° C., like 60° C. to 80° C.

If desired, the adhesion material according to the present invention may contain additional ingredients, like antibacterial agents and/or pigments and/or drugs and/or fillers and/or polymers and/or nanoparticles.

The adhesive or adhesion material according to the present invention is in particular a cement for dental prostheses or brackets selected from phosphatebased cement, in particular, zinc phosphate or silicophosphate, a polycarboxylate-based cement, in particular, zinc polycarboxylate, ionomer, or HARVARD cement (zinc phosphate).

The adhesion material according to the present invention is in particular for use in adhesion of dental prosthesis, like restorations, or brackets, in particular, means and devices present in oral cavities. However, the adhesive material according to the present invention may also be used as adhesive for implants in other parts of an individual requiring adhesion of implanted devices.

The adhesion material according to the present invention is characterised in that a permanent fixation of a second element on a first element, optionally with an intermediate element is envisaged. However, the second element, like the restoration or bracket/dental application may be removed easily by applying energy-rich radiation, thus, increasing locally the temperature of the phase-change material. As a consequence weakening of the adhesion strength and, consequently, allowing removing the implant easily without destruction of the implanted material is possible.

The capsule engulfing the phase-change material may be for example a capsule consisting of the silica wall with integrated $Au/SiO_2$ core/shell (gold core/silica shell) nanoparticles. The amount of the $Au/SiO_2$ core/shell nanoparticles in the capsule wall may be varied from 2 to 20 wt.-%. The shape of the gold core may vary from spherical to cylindrical. The thickness of the capsule may vary from 50 to 800 nm based on the desired purposes. Some functional groups may be integrated into the capsule wall to ensure formation of chemical bonds between capsules and cement matrix. The capsule itself may be destroyed when applying sufficient energy to heat the phase-change material above the phase transition temperature. Alternatively, the phase-change from e.g. solid to liquid does not destroy the capsule but weaken the adhesion material in a way allowing easy removal of the adhered material.

Not to be bound by theory, the FIGS. 1 and 2 are schemes outlining the principle of the present invention.

The adhesion material according to the present invention may be produced easily. That is, conventional adhesion materials may be modified by adding the encapsulated phase-change material. The amount, size and other properties of the encapsulated phase-change material may be determined easily by a skilled artisan.

The present invention relates further to a method of removing a second element, like a restoration, in particular, a crown or bridge, fixed on a first element, like an implant or teeth, or a bracket fixed on teeth, comprising the step of irradiating the adhesion material according to the present invention adhering the implant or bracket, with sufficient energy to heat the phase-change material present in the adhesion material according to the present invention, above the phase transition temperature of the phase-change material. Heating of the phase-change material allows to weak the adhesion strength of the adhesion material according to the present invention. Thus, the second element, like the dental prosthesis or a bracket can be removed easily. In addition, the dental prosthesis or bracket is not destroyed and can be re-used after cleaning and, optionally, disinfection.

It is preferred that irradiation is effected by laser light, UV-VIS or NIR, magnetic field, ultrasound or microwaves. The source of irradiation depends on the characteristics of the implant.

In addition, the present invention relates to a dental implant restoration system comprising the adhesion material according to the present invention. Said dental implant restoration system may further comprise the second elements and the optional intermediate elements, like restorations, e.g. crowns, bridges, abutments as well as the first elements, like implant bodies. The dental implant restoration system refers in addition to dental braces including brackets to be fixed on the teeth.

The adhesion material according to the present invention is suitable for fixation of all porcelain crowns but also off porcelain-fused-to-metal (PFM) crowns and other types of dental prostheses.

The kit for permanent fixation on elements in a body, like implants allowing removal of the means and devices fixed on said elements comprises the adhesion material according to the present invention. The kit as well as the system described above may comprise further means and devices for applying or depositing the adhesion material on the elements, like the implant. The adhesion material is preferably provided in a storable form as known in the art.

The adhesion material according to the present invention may be provided in a two-part form. That is, the adhesion material may be in a form of a first preparation of the adhesion material without the encapsulated phase-change material and a second separately stored preparation of the encapsulated phase-change material.

In the following, the principle underlying the present invention is described.

In FIG. 1 the encapsulated phase-change material is shown. The core comprises phase-change material, e.g. sodiumsulfate decahydrate or polyethylenglycol polymer or wax and the encapsulation material is composed of silica particles containing Au. Alternatively, the Au may be present in the core of said capsules or may be present in both, the core and the wall. Said encapsulated phase-change material is incorporated into dental cement being randomly distributed therein. The encapsulated phase-change material is provided in an amount sufficient to weaken or even crack or destroy the adhesion material when applying energy to allow phase-change of said phase-change material.

In FIG. 2, the weakening and, in the end, the destruction of the adhesion material is shown. The cement matrix containing the encapsulated solid phase-change material (PCM) is irradiated with energy, e.g. laser light. Eventually, the expansion of the PCM allow to build crack formation under load as shown in the lower scheme. Thus, weakening and, eventually, cracking and destruction of the adhesion material is achieved.

As used herein, the terms "comprising", "comprises", "containing", or "contains" include the embodiments of "consisting of" or "consists".

The invention claimed is:

1. A dental or orthodontic adhesion composition, comprising:
   one or more capsules, wherein said one or more capsules includes silica;
   a phase-change material having a phase transition temperature above 40° C., wherein said phase-change material is encapsulated within said one or more capsules to form an encapsulated phase change material; and
   an adhesion material, wherein said encapsulated phase change material is positioned within said adhesion material, and wherein said phase change material is maintained separate from said adhesion material at least prior to exposure to energy by said one or more capsules,
   wherein said adhesion material and said encapsulated phase change material are configured such that upon exposure to energy sufficient to cause said phase change material to undergo a phase change, said adhesion, material will soften,
   wherein said adhesion material with said encapsulated phase change material is formulated for cosmetic or medicinal use in individuals for dental or orthodontic applications.

2. The dental or orthodonic composition of claim 1 wherein said phase transition temperature of said phase-change material is above 55° C.

3. The dental or orthodonic composition of claim 1, wherein said adhesion material is selected from the group consisting of a permanent cement or polymeric adhesion material.

4. The dental or orthodontic composition of claim 1, wherein said phase-change material is selected from the group consisting of polymers, inorganic salts, or organic materials.

5. The dental or orthodontic composition of claim 1 further comprising one or more of anti-bacterial agents, pigments, drugs, fillers, polymers, and nanoparticles.

6. The dental or orthodontic composition of claim 1 wherein the adhesion material is selected from the group consisting of phosphate-based cement, and polycarboxylate-based cement, and glass ionomer.

7. The dental or orthodontic composition of claim 6 wherein the adhesion material is a polycarboxylate-based cement and said polycarboxylate-based cement is zinc polycarboxylate.

8. The dental or orthodontic composition of claim 4 wherein the phase change material is a polymer selected from the group consisting of polyethyleneoxide polymers and polyethylene glycol polymers.

9. The dental or orthodontic composition of claim 4 wherein the phase change material is a salt hydrate.

10. The dental or orthodontic composition of claim 4 wherein the phase change material is a wax.

11. The dental or orthodontic composition of claim 1 wherein said one or more capsules have a size of 10 nm to 20 μm in diameter.

12. The dental or orthodontic composition of claim 1 wherein said one or more capsules have a shape that is selected from the group consisting of spherical and cylindrical.

13. The dental or orthodontic composition of claim 1 wherein said one or more capsules have a thickness ranging from 50 to 800 nm.

14. The dental or orthodonic composition of claim 1 wherein said energy is selected from the group consisting of laser light, ultraviolet light, visible light, near infrared, magnetic field, ultrasound and microwaves.

* * * * *